US00PP11343P

United States Patent [19]

Koppe

[11] Patent Number: Plant 11,343

[45] Date of Patent: Apr. 11, 2000

[54] BEGONIA PLANT NAMED 'BAZAN'

[75] Inventor: Lubbertus H. Koppe, Ermelo, Netherlands

[73] Assignee: Koppe Veredeling B.V., Ermelo, Netherlands

[21] Appl. No.: 09/112,647

[22] Filed: Jul. 9, 1998

[51] Int. Cl.[7] ..... A01H 5/00

[52] U.S. Cl. ..... Plt./349

[58] Field of Search ..... Plt./344, 348, 349

[56] References Cited

U.S. PATENT DOCUMENTS

P.P. 7,404 12/1990 Man ..... Plt./348
P.P. 9,523 4/1996 Koppe ..... Plt./349

*Primary Examiner*—Howard J. Locker
*Assistant Examiner*—Wendy A Baker
*Attorney, Agent, or Firm*—C. A. Whealy

[57] ABSTRACT

A distinct variety of Begonia plant named 'Bazan', characterized by its large pink flowers that are about 7 cm in diameter; fully double flowers with numerous tepals per flower; upright and spreading plant form; freely branching; and excellent postproduction longevity.

2 Drawing Sheets

BACKGROUND OF THE INVENTION

The present invention relates to a new and distinct variety of Begonia plant, botanically known as *Begonia×hiemalis*, commercially known as Elatior Begonia, and hereinafter referred to by the name 'Bazan'.

The new Begonia was discovered by the inventor in a controlled environment in Ermelo, The Netherlands, in June, 1995, as a naturally-occurring mutation of *Begonia×hiemalis* 'Barkos', disclosed in U.S. Plant Pat. No. 9,523. The new Begonia was observed as a single plant in a group of flowering plants of the parent variety. The selection of this plant was based on its different flower color.

Asexual reproduction of the new Begonia by leaf and terminal cuttings taken in a controlled environment in Ermelo, The Netherlands, has shown that the unique features of this new Begonia are stable and reproduced true to type in successive generations.

SUMMARY OF THE INVENTION

The variety 'Bazan' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bazan'. These characteristics in combination distinguish 'Bazan' as a new and distinct Begonia:

1. Pink flowers that are about 7 cm in diameter.
2. Fully double flowers with numerous tepals per flower.
3. Upright and spreading plant form.
4. Freely branching plant habit.
5. Excellent postproduction longevity.

In side-by-side comparisons conducted by the inventor in Ermelo, The Netherlands, plants of the new Begonia differ from plants of the parent cultivar Barkos in flower color as plants of the cultivar Barkos have orange-red (R.H.S. 44A) flowers.

BRIEF DESCRIPTION OF THE PHOTOGRAPHS

The accompanying colored photographs illustrate the overall appearance of the new Begonia, showing the colors as true as it is reasonably possible to obtain in colored reproductions of this type.

The photograph on the first sheet comprises a top perspective view of a typical flowering plant of 'Bazan'.

The photograph on the second sheet comprises a close-up view of typical leaves (top) and typical flowers (bottom) with lower surfaces on the left and upper surfaces on the right. Flower and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Ermelo, The Netherlands, under commercial practice in a glass-covered greenhouse. Average day and night temperatures were 20° C. during the first three to four weeks then lowered to an average day and night temperature of 19° C. until flowering. Four weeks after planting, two weeks of long nyctoperiods were given followed by short nyctoperiods of eight hours. Measurements and numerical values represent averages for typical flowering plants.

Botanical classification: *Begonia×hiemalis* 'Bazan'.
Commercial classification: Elatior Begonia.
Parentage: Naturally-occurring mutation of *Begonia×hiemalis* 'Barkos', disclosed in U.S. Plant Pat. No. 9,523.
Propagation:
- *Type.*—Terminal cuttings.
- *Time to rooting.*—About 5 weeks with soil temperatures of 20° to 22° C.
- *Rooting habit.*—Fine, fibrous, well-branched, and spreading; plants do not form tubers.

Plant description:
- *Plant form.*—Upright and spreading potted plant; freely branching with good stem and stem base strength. Flowers are fully double and abundant. Plants flower continuously.

*Growth habit.*—Moderate growth rate, vigorous. Suitable for 9 to 15-cm containers. Under optimal environmental and cultural conditions, usually 10 to 12 weeks are required to produce proportional 13-cm potted plants from terminal cuttings. Vegetative shoots are formed at basal nodes and flowering shoots are formed at upper nodes.

*Plant height.*—About 28 cm.

*Leaves.*—Arrangement: Simple, alternate. Length: About 11.5 cm. Width: About 11.5 cm. Shape: Asymmetrical, more or less reniform. Apex: Acute to acuminate. Base: Cordate. Margin: Doubly serrate. Texture: Slightly pubescent. Petiole length: About 6 cm. Color: Young and fully expanded foliage, upper surface: 147A. Young and fully expanded foliage, lower surface: 147B to 147C. Venation, upper and lower surfaces: 144D. Petiole: 144D with anthocyanin coloration.

Flower description:

*Flowering habit.*—Large and fully double flowers with numerous tepals arranged in axillary cymes. Usually three to six flowers per cyme. Many cymes in flower simultaneously. Flowering continuous.

*Natural flowering season.*—Plants will flower year around regardless of nyctoperiod, however plants flower earlier and more abundantly from mid-February until November in the Northern Hemisphere.

*Flowers.*—Shape: Rounded. Diameter: About 7 cm. Depth (height): About 3 cm.

*Flower buds.*—Length: About 2 cm. Diameter: About 1.5 cm. Color, outer surface: 50A becoming lighter, 54A, with development.

*Tepals.*—Arrangement: Rosette. Shape: Very broadly cordate with rounded apex. Margin: Entire to slightly crenate. Quantity per flower: Usually about 35 per flower. Size: Outer tepals: Length: About 2.75 cm. Width: About 3.5 cm. Inner tepals: Length: About 2 cm. Width: About 2 cm. Texture: Smooth, satiny, glabrous. Color: When opening: 54A. Fully opened, upper surface: 54A, fading to 54B, then to 54C with subsequent development. Fully opened, lower surface: 54B.

*Peduncles.*—Angle: Erect to bent. Length: About 9 cm. Texture: Slightly pubsecent. Color: 144D with anthocyanin coloration.

*Bracts.*—Arrangement: Two, opposite. Shape: Broadly cordate. Apex: Rounded to slightly mucronate. Margin: Serrate. Color: 144D with anthocyanin coloration.

*Reproductive organs.*—Stamens: None observed. Pistils: None observed.

Postproduction longevity:

*Individual flowers.*—Generally about 2 to 3 weeks.

*Whole plants.*—About 6 weeks under interior conditions.

Disease resistance: Resistance to diseases common to Begonia has not been noted.

Seed production: Seed production has not been observed as reproductive organs are not formed.

It is claimed:

1. A new and distinct variety of Begonia plant named 'Bazan', as illustrated and described.

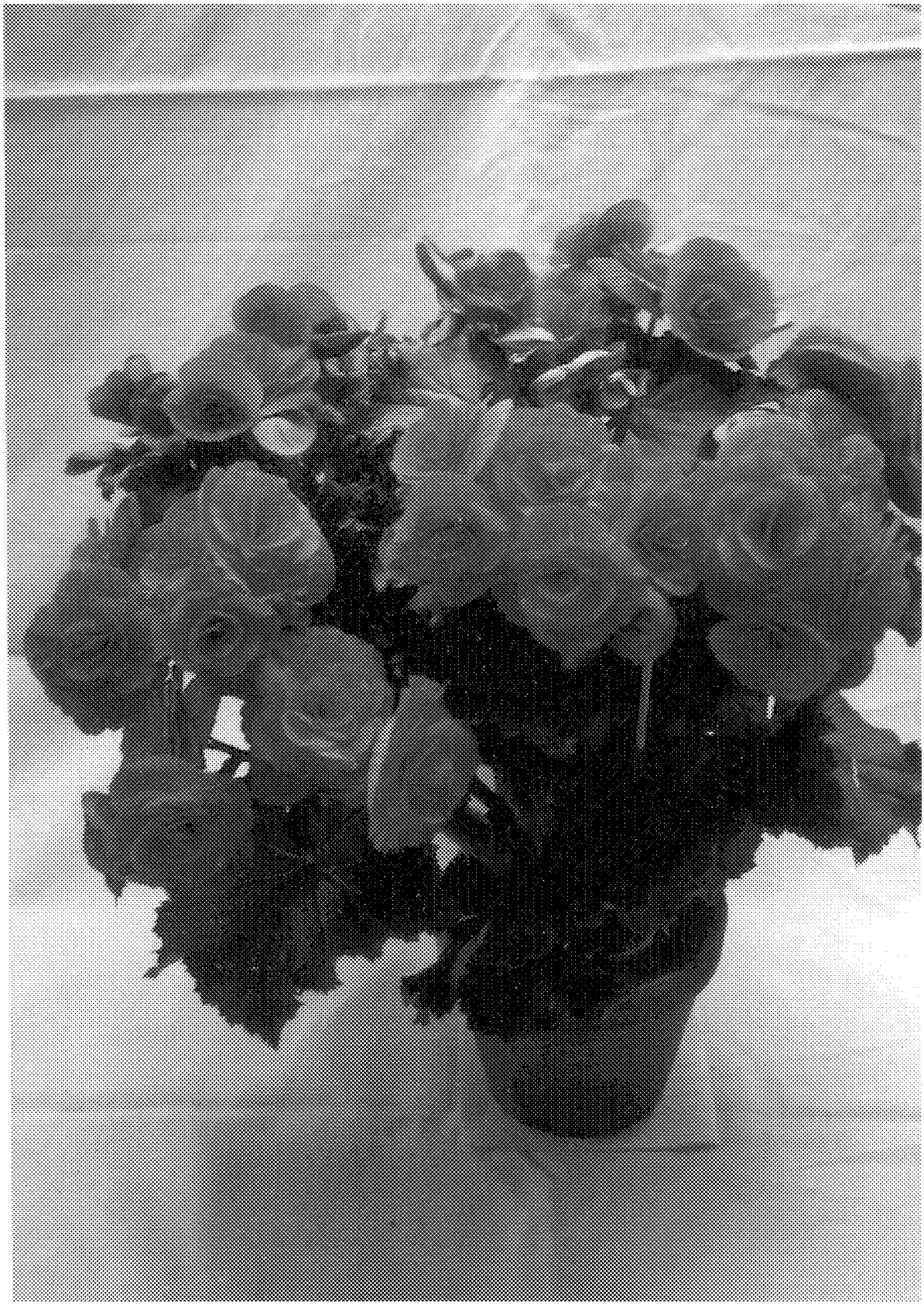

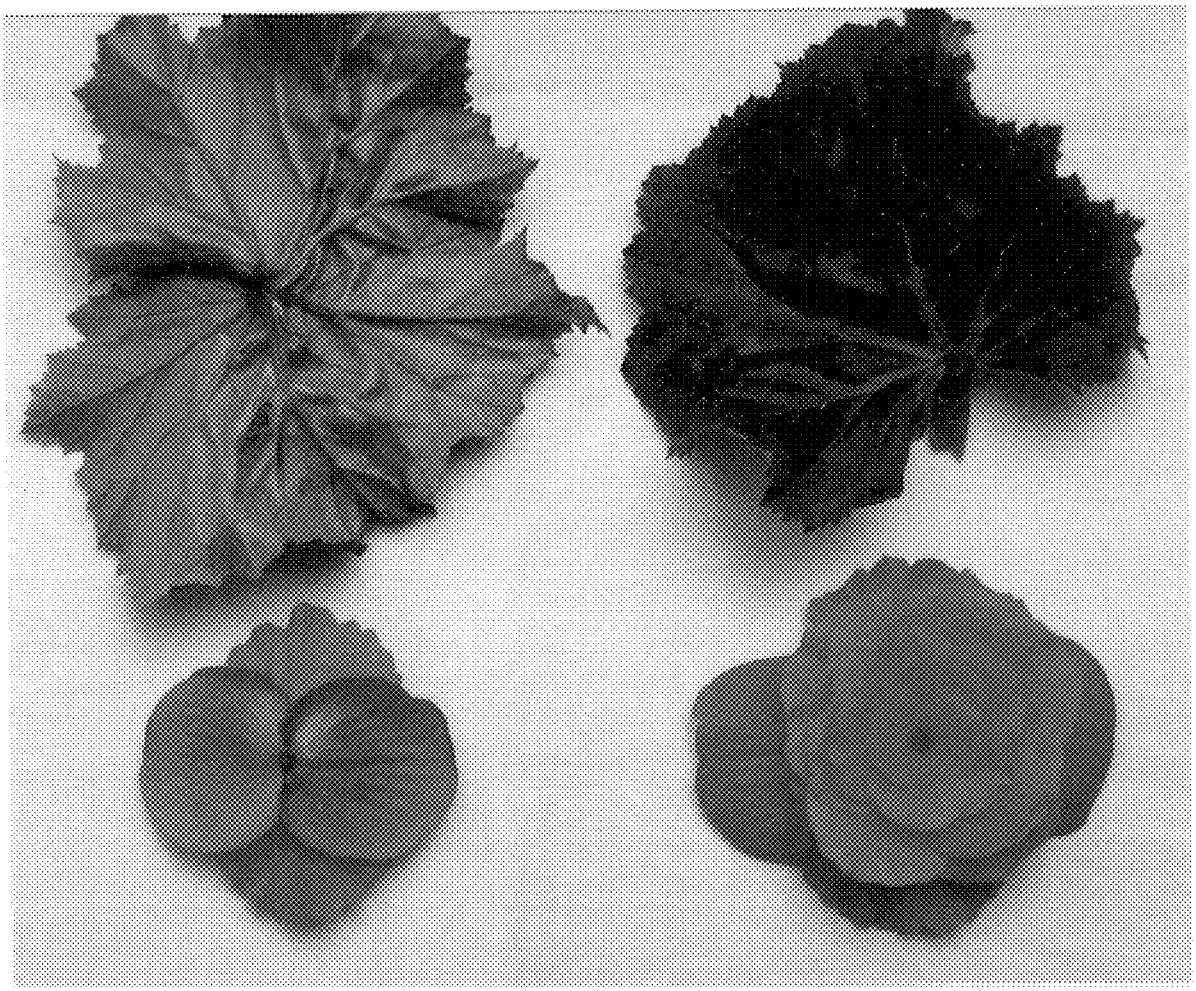

* * * * *